(12) United States Patent
Busiashvili

(10) Patent No.: US 8,992,972 B1
(45) Date of Patent: *Mar. 31, 2015

(54) CAPSULE FOR SUBLINGUAL AND GASTRO-INTESTINAL DELIVERY OF A LIQUID MEDICATION IN A SINGLE VOLUME LIMITED DOSE

(71) Applicant: Yuri Busiashvili, Pacific Palisades, CA (US)

(72) Inventor: Yuri Busiashvili, Pacific Palisades, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/450,650

(22) Filed: Aug. 4, 2014

Related U.S. Application Data

(63) Continuation-in-part of application No. 14/291,927, filed on May 30, 2014, now Pat. No. 8,865,209.

(51) Int. Cl.
*A61J 3/07* (2006.01)
*A61K 9/48* (2006.01)

(52) U.S. Cl.
CPC .................................. *A61K 9/4808* (2013.01)

USPC .......................................... 424/454; 424/451

(58) Field of Classification Search
USPC .................................................. 424/454, 451
See application file for complete search history.

(56) References Cited

U.S. PATENT DOCUMENTS

| | | | | |
|---|---|---|---|---|
| 5,179,801 | A * | 1/1993 | Babchuk et al. | 49/58 |
| 5,560,490 | A * | 10/1996 | Chawla | 206/539 |
| 7,279,457 | B2 | 10/2007 | Pohl et al. | |
| 8,361,497 | B2 | 1/2013 | Miller | |
| 2002/0004067 | A1 * | 1/2002 | Crison et al. | 424/451 |

* cited by examiner

*Primary Examiner* — Gina Justice
(74) *Attorney, Agent, or Firm* — Ralph D. Chabot

(57) ABSTRACT

A capsular design is disclosed for self-administered delivery of a pre-determined amount of liquid medication. The capsular design can be constructed as having either a single piece or two piece capsular wall construction where a portion of the liquid medication contained within can be administered sublingually and the remaining portion can be subsequently swallowed for gastro-intestinal absorption.

9 Claims, 3 Drawing Sheets

CAPSULE FOR SUBLINGUAL AND GASTRO-INTESTINAL DELIVERY OF A LIQUID MEDICATION IN A SINGLE VOLUME LIMITED DOSE

CROSS REFERENCE TO RELATED APPLICATIONS

This application claims the benefit of: U.S. patent application bearing Ser. No. 14/291,927 filed May 30, 2014 the contents of which are hereby incorporated by reference herein in its entirety for all purposes.

BACKGROUND OF THE INVENTION

Oral delivery of medications is one of the most frequent techniques utilized for delivering medication to the body. One of the most popular delivery mechanisms is the capsule. The background of U.S. Pat. No. 8,361,497 issued to Miller provides a detailed description into the history and present techniques for capsule manufacture and is hereby incorporated by reference.

Capsules containing medication for oral intake are usually swallowed for delivery of the medication to the stomach, where the capsule dissolves within 20 to 30 minutes and the medication is absorbed into the bloodstream.

A two piece capsule design is typically used for delivering medication in a solid form such as a fine powder or pellets. One or both portions of this capsule design are made of a material which quickly becomes mollified when coming in contact with liquid, such as water or gastric juice.

With respect to capsular delivery of liquid medication such as nitroglycerin, the capsule design is sealed and having no orifices. This type of design essentially encapsulates the medication until the capsular wall is dissolved in the gastrointestinal tract; thereafter releasing the medication into the body for absorption. The composition of the capsular wall used for liquid containment is different than that used for medication in a non-liquid form.

SUMMARY OF THE INVENTION

Described herein is a capsular design used for self-administration of medication in medical emergencies whereby a portion of the total volume of liquid medication contained in a capsule can be applied to the sublingual area of a human and the remaining medication in the capsule can thereafter be swallowed for absorption in the gastro-intestinal tract. The therapeutic amount of liquid medication addressed by my invention has a volume of at least 0.2 ml and less than 1 ml and more preferably, less than 0.5 ml.

Accordingly, my invention describes a device containing a therapeutic liquid medication in a single volume limited dose partially delivered sublingually and partially delivered to the gastro-intestinal tract.

Described below are capsular embodiments capable of delivering a portion of the medication contained therein sublingually and the remaining portion for ingestion in the gastro-intestinal tract. The capsular embodiments described below include single piece and two piece structures. One critical feature of my capsular design is that the capsular wall, particularly along the longitudinal axis, in response to a sufficient force applied to the exterior wall such as that applied by a person's thumb and forefinger, will sufficiently deform or collapse for discharging an amount of medication for sublingual absorption.

A benefit to my capsular designs is the ability to deliver a maximal allowable amount of a liquid medication for a single use; partially under the tongue and the remaining liquid medication in the capsule to the stomach and intestines. The combination of absorption sublingually followed by absorption within stomach and/or intestines allows rapid absorption as well as a more prolonged duration of absorption of the medication to the blood stream.

Medication contemplated for use by my invention includes concentrated liquid medication forms such as Nifedipine and Nitroglycerin. The capsule may be provided in a sealed package which requires the capsule to be pushed through a thin film backing for additional protection. This type of package is commonly available. Because the medication contemplated by my invention is liquid, it is necessary to carefully select the material that will comprise the capsule wall so the liquid medication contained within cannot react and dissolve or mollify the capsule wall.

The intended purpose of my invention is to deliver a portion of the therapeutic amount sublingually which will alleviate the patient's acute condition in as short a time as one minute and thereafter ingest the remaining portion of the therapeutic amount which will provide a more prolonged duration of the medication in the human's bloodstream.

It is to be understood that my invention will work only with those medications which are liquid in a concentrated form in which the therapeutic amount can be retained in a capsule. A container having liquid medication in excess of 1 ml discharged completely into the mouth would tend to be comingled with a human's saliva and swallowed defeating the purpose of my invention which is to deposit no more than a few drops (i.e. preferably no more than 0.5 ml) of medication underneath the tongue for sublingual absorption and then the portion remaining in the capsule swallowed to achieve a longer lasting effect. Since sublingual absorption results in medication entering the bloodstream almost instantaneously, sublingual absorption in combination with gastro-intestinal absorption which takes about 20-30 minutes should result in a longer lasting therapeutic effect.

In one embodiment of my two piece capsule design, the capsule comprises a base and cap. Preferably, this embodiment includes a pair of contralateral apertures on opposing sides of each capsule half, i.e. one aperture on the cap and the other on the base, where the assembled capsule has a first position in which the aperture pair are offset from each other. The base and cap are rotatable relative to each other and can be rotated to a second position where the apertures are aligned forming an opening for a portion of the medication located within the capsule to be discharged for sublingual delivery. With respect to the sidewall of the base and cap, one has an inside diameter slightly greater than the outside diameter of the other. The sidewalls overlap each other by a short length, approximately 1.5 mm-5 mm as is well known by those having skill in the art. This overlap of sidewalls is defined as an overlap area.

The cross-sectional area of the holes is collectively of sufficient size for discharge of the medication approximately 1 mm in diameter. The holes on both the cap and base are located in the overlap area.

Once the opening is formed, the capsule can be squeezed to discharge a portion of the therapeutic amount of medication. The discharge portion will most likely be no more than a few drops which will be a quantity sufficient to maintain in the sublingual area under the tongue. The capsule can thereafter be swallowed which will result in the remainder of the therapeutic amount left within the capsule to be absorbed in the stomach and/or intestines.

Rather than use of a capsule having separate cap and base portions, a single-piece or uniform cap structure could also be utilized. In a preferred structure, the capsule would have a sufficiently thin sidewall to be collapsible in response to an inward force applied by a thumb and forefinger grasping the capsule. The capsule would further incorporate a closed opening. The closed opening could involve any number of designs such as a nipple; or include a removable obstruction where an aperture is initially sealed using a removable plug or adhesive strip. Once the obstruction is removed, the forefinger and thumb of a single hand would grasp the capsule, position the closed opening above the sublingual area of a human's mouth and apply pressure to the capsule sidewall causing a portion of the therapeutic medication within the capsule to discharge onto the sublingual area. Another design would be to incorporate a thinner wall section located at the end of the capsule to act as a rupture disc which, in response to external force applied to the capsule body would fail and permit a portion of the liquid medication to be discharged.

For a nipple design outlet from the capsule, the nipple would be located at one end having an enlarged capsule wall thickness with through and through fissures as tributaries confluent towards the apex of the nipple. The liquid medication travels via small passages connecting pockets or miniature lakes where liquid can accumulate. A portion of the liquid medication can be discharged when pressure is applied with the thumb and forefinger to the body of the capsule as illustrated in FIG. 6c.

DESCRIPTION OF THE PREFERRED EMBODIMENT

The figures provided herein are not drawn to scale and are provided for representational and instructional purposes.

Figure 1A:
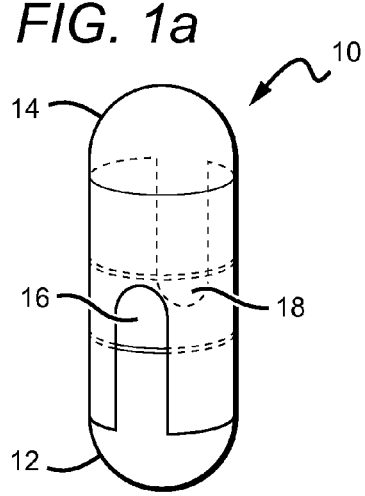
FIG. 1a is a perspective view of a capsule made according to my invention in a closed position.
Figure 2:
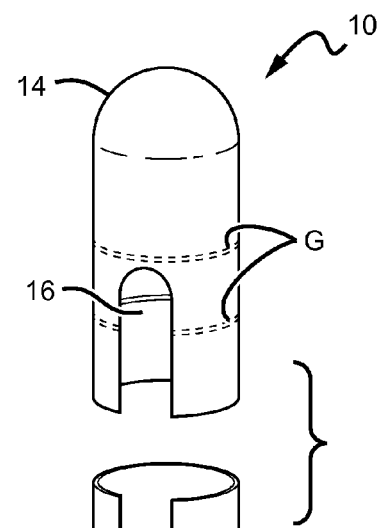
FIG. 2 is an exploded view of the capsule illustrated in FIGS. 1a and 1b.
Figure 2:
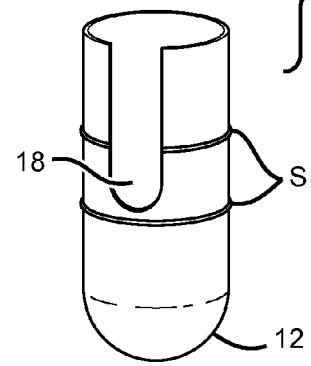

FIG. 1a illustrates an enlarged view of a capsule 10 made according to my invention in a closed position. Referring to the exploded view of FIG. 2, capsule 10 consists of two halves, a base 12 and a cap 14, which overlap each other by approximately 2-4 mm Base and cap can each be described as an open mid-segment cylinder each having a slightly different circumferential diameter from the other. A de minimis annular region exists when base 12 and cap 14 are fitted together as shown in FIG. 1a to prevent leakage of the liquid medication contained within capsule 10. Base 12 has orifice 18 extending from its open end and further includes a pair of spaced apart circumferential ridges S in parallel relation. Cap 14 has orifice 16 extending from its open end and further includes a pair of spaced apart circumferential grooves G in parallel relation. When base 12 and cap 14 are fitted together, as shown in FIG. 1a, a respective ridge S will be slidably fitted in a respective groove G to act as a seal. Orifices 16 and 18 are originally in a closed position, preferably contra lateral to one another. Capsule 10 is filled with a therapeutic amount of liquid medication (not shown).

Figure 1B:
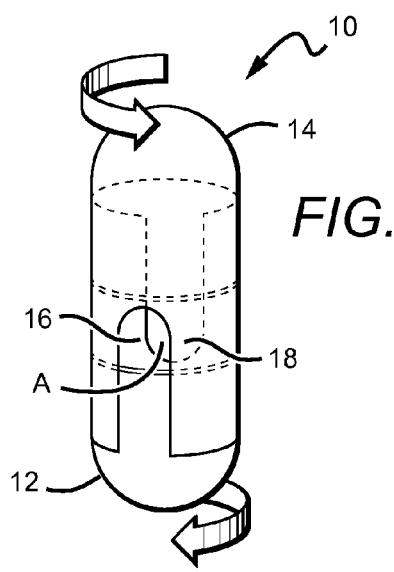
FIG. 1b is a perspective view of a capsule made according to my invention rotated toward an open position.

When a medical emergency occurs requiring the medication to be administered, capsule 10 is rotated from its first position illustrated in FIG. 1a to a second position in which orifaces 16 and 18 are aligned to form opening A. FIG. 1b illustrates the rotation of base 12 and cap 14 toward the second position.

Figure 3:
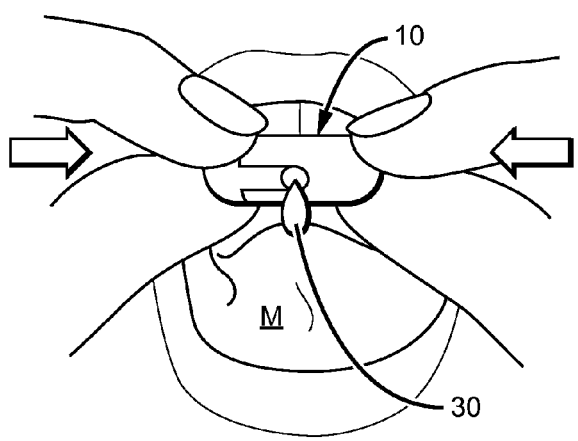
FIG. 3 is a perspective view of how the medication is delivered from the capsule to the sub-lingual area.

A portion of the therapeutic amount of medication 30 is discharged from capsule 10 by applying squeezing the capsule as represented in FIG. 3. Medication is deposited onto the sublingual area of the mouth M. The medication remaining within capsule 10 is swallowed for absorption by the stomach and/or intestines.

Figure 4A:
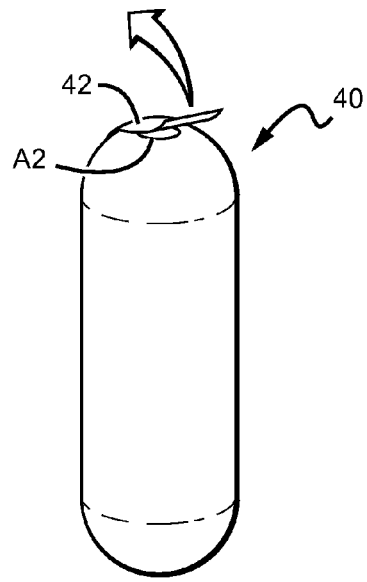
FIG. 4a is a first alternative embodiment with the aperture located on one end of the capsule.
Figure 4B:
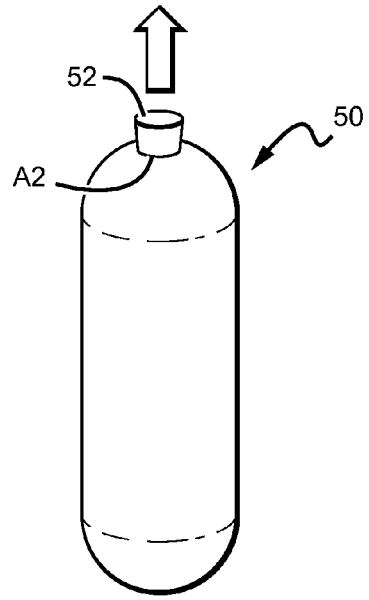
FIG. 4b is a second alternative embodiment with the aperture located on one end of the capsule.
Figure 4C:
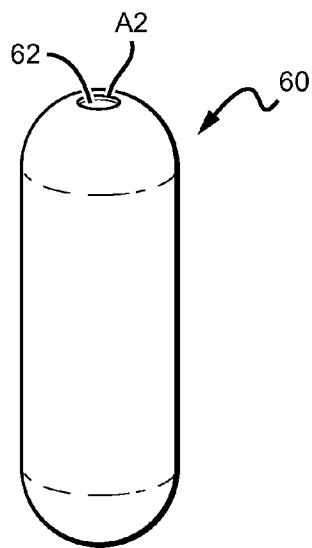
FIG. 4c is a third alternative embodiment with the aperture located on one end of the capsule.

Referring to FIGS. 4a, 4b and 4c, three single piece capsular wall structures are presented which illustrate variations of a removable obstruction. Each structure utilizes at least one aperture for the discharge of liquid medication. FIG. 4a illustrates a capsule 40 having a removable adhesive strip 42 which covers aperture A2. FIG. 4b illustrates a capsule 50 having a removable plug 52 which is positioned within aperture A2 and held in position by frictional engagement with the surrounding capsular wall. FIG. 4c illustrates a capsule 60 having a rupture disc 62; essentially a reduced wall area integral with the surrounding capsular wall which will rupture upon sufficient pressure applied to the capsule sidewall thus creating aperture A2.

Figure 5:
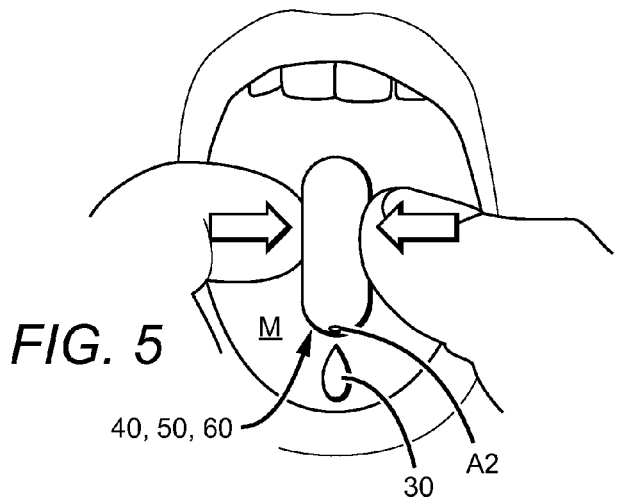
FIG. 5 is a perspective view of the capsule being grasped by the thumb and forefinger of one hand.

A portion of the therapeutic amount of medication 30 is discharged from capsule 40, 50, or 60 by applying force to the outer wall as shown in FIG. 5. Medication is deposited onto the sublingual area of the mouth M. The medication remaining within capsule 40, 50, or 60 is swallowed for ingestion in the stomach and/or intestines.

Figure 6A:
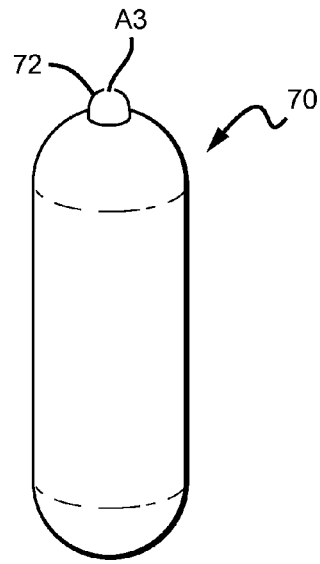
FIG. 6a is a fourth alternative embodiment that uses a nipple-type orifice.
Figure 6B:
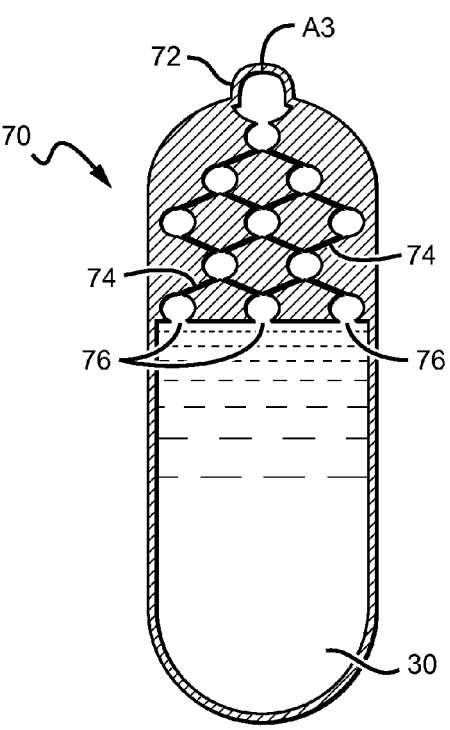
FIG. 6b is an interior view of the capsule illustrated in FIG. 6 shown in a condition before liquid medication is discharged.
Figure 6C:
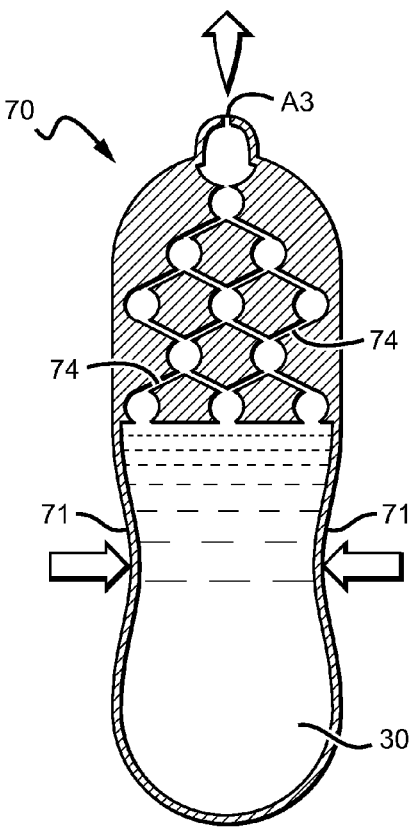
FIG. 6c is an interior view of the capsule illustrated in FIG. 6 shown in a condition as liquid medication is being discharged.

FIGS. 6a, 6b and 6c illustrate a fourth alternative single piece capsular wall construction 70 which has a sidewall 71 and a nipple 72 having orifice A3 for discharge of liquid medication 30. Orifice A3 presented in FIGS. 6a and 6b is originally a slit in the capsule wall at one end and does not open until pressure is applied to the capsule body as shown in FIG. 6c whereby the pressure within capsule 70 causes orifice A3 to open. When pressure is applied as shown by arrows 71, pressure builds within capsule 70 and causes the slit to rupture creating orifice A3. Referring to FIG. 6b, capsule 70 has an interior which is partially filled with liquid medication 30. Also contained within the capsule interior is at least one pathway preferably having a plurality of interconnected channels 74 operatively connected to aperture A3 for discharge of a portion of the liquid medication. Channels 74 are initially in a collapsed or semi-folded condition which prevents liquid flow. Inlet ports 76 are provided for entry of the medication into channels 74 and pockets. Upon capsule 70 being pinched as illustrated in FIG. 6c, pressure builds within the interior of capsule 70 which causes a portion of liquid medication 30 to begin flowing through channels 74 and the pockets and exit at orifice A3. The user would take capsule 70 and pinch along sidewall 71 as shown in FIG. 6c to apply a sufficient pressure force upon the sidewall of the capsule as illustrated by the arrows and discharge the portion of liquid medication for placement under the tongue for sublingual delivery

I claim:

1. A capsule for providing a portion of therapeutic medication for sublingual absorption and the remainder of the therapeutic liquid medication for gastro-intestinal absorption, the capsule comprising a single-piece exterior wall structure dissolvable in the gastro-intestinal tract of a human, said structure containing a pre-determined volume of therapeutic liquid medication, said structure further comprising at least one aperture for discharge of a portion of said therapeutic liquid medication, and, a removable adhesive strip disposed upon a portion of the exterior wall of said capsule which surrounds said at least one aperture to prevent discharge of said therapeutic medication.

2. A capsule for providing a portion of therapeutic liquid medication for sublingual absorption and the remainder of the therapeutic liquid medication for gastro-intestinal absorption, the capsule comprising a single-piece exterior wall structure dissolvable in the gastro-intestinal tract of a human, said structure containing a pre-determined volume of therapeutic liquid medication, said structure further comprising at least one aperture for discharge of a portion of said therapeutic liquid medication, and, a removable plug inserted into a respective said at least one aperture whereby said removable plug frictionally engages the exterior wall surrounding said at least one aperture.

3. A capsule for providing a portion of therapeutic liquid medication for sublingual absorption and the remainder of the therapeutic liquid medication for gastro-intestinal absorption, the capsule comprising a single-piece exterior wall structure dissolvable in the gastro-intestinal tract of a human, said structure containing a pre-determined volume of therapeutic liquid medication, said capsule further comprising a rupture disc which, when in a non-ruptured condition, is integral with said exterior wall structure that seals said therapeutic liquid medication within said capsule; and, when said rupture disc is in a ruptured condition, an aperture is formed for discharge of a portion of said liquid therapeutic medication.

4. The capsule of claim 1 where said therapeutic liquid medication is Nifedipine.

5. The capsule of claim 1 where said therapeutic liquid medication is Nitroglycerin.

6. The capsule of claim 2 where said therapeutic liquid medication is Nifedipine.

7. The capsule of claim 2 where said therapeutic liquid medication is Nitroglycerin.

8. The capsule of claim 3 where said therapeutic liquid medication is Nifedipine.

9. The capsule of claim 3 where said therapeutic liquid medication is Nitroglycerin.

* * * * *